United States Patent [19]
Haynes et al.

[11] Patent Number: 5,246,418
[45] Date of Patent: Sep. 21, 1993

[54] IONTOPHRESIS SYSTEM HAVING FEATURES FOR REDUCING SKIN IRRITATION

[75] Inventors: John L. Haynes, Chapel Hill; Burton H. Sage, Jr., Raleigh, both of N.C.

[73] Assignee: Becton Dickinson and Company, Franklin Lakes, N.J.

[21] Appl. No.: 808,754

[22] Filed: Dec. 17, 1991

[51] Int. Cl.$^5$ .............................................. A61N 1/30
[52] U.S. Cl. ........................................ 604/20; 607/152
[58] Field of Search ............. 604/20; 128/419 R, 783, 128/798, 803, 640

[56] References Cited

U.S. PATENT DOCUMENTS

| | | |
|---|---|---|
| 4,141,359 | 2/1979 | Jacobsen et al. . |
| 4,164,226 | 8/1979 | Tapper . |
| 4,211,222 | 7/1980 | Tapper . |
| 4,292,968 | 10/1981 | Ellis ........................................ 604/20 |
| 4,722,726 | 2/1988 | Sanderson et al. ................... 604/20 |
| 4,725,263 | 2/1988 | McNichols et al. . |
| 4,764,164 | 8/1988 | Sasaki . |
| 5,084,006 | 1/1992 | Lew et al. ............................ 604/20 |

OTHER PUBLICATIONS

Article by Nancy A. Monteiro-Riviere in *Fundamental Applied Technology*, entitled "Altered Epidermal Morphology Secondary to Lidocaine Iontophoresis: In Vivo and In Vitro Studies in Porcaine Skin", vol. 15, pp. 174–185 (1990).

*Primary Examiner*—Lee S. Cohen
*Assistant Examiner*—Brian L. Casler
*Attorney, Agent, or Firm*—Hoffmann & Baron

[57] ABSTRACT

An iontophoresis drug delivery system includes a device which is attachable to the skin of an animal and having a drug reservoir, an electrolyte reservoir, and electrodes electrically communicating with the reservoirs and with the skin of the animal. An electronic circuit for controlling the rate or amount of current or voltage applied to the electrodes of the device includes a constant voltage and current generator, and a switching circuit for switching between applying either a constant current to the electrodes or a constant voltage. Current and voltage sensors are attached to the electrodes and provide feedback signals which are compared with predetermined threshold signals to control through feedback the amount of constant voltage and constant current applied to the electrodes.

26 Claims, 6 Drawing Sheets

IONTOPHRESIS SYSTEM HAVING FEATURES FOR REDUCING SKIN IRRITATION

FIELD OF THE INVENTION

This invention relates to a system and method for iontophoretic drug delivery having features for reducing irritation to the skin of an animal and more particularly, to a system for delivery of power during iontophoretic drug delivery in a sequence for reducing skin irritation.

BACKGROUND OF THE INVENTION

Iontophoresis is gaining increased acceptance as an effective method for application of ionic agents or ionic drugs through the skin of an animal. Iontophoresis can be defined as the electrically driven application of drugs or medications, in their ionic form, to the surface tissues of an animal. The application of electric current causes migration of ions into the tissue wherein such migration is proportional to the quantity of current applied through the iontophoretic system. Skin irritation can occur during iontophoretic drug delivery. Efforts to minimize irritation have been directed to regulating the level of current, improving the electrical connection of the electrode with the skin and reducing the hydrolysis of water in the ionic medication. Irritation of the skin may be subjective wherein the iontophoretic electrode delivers so much power that it causes extreme discomfort to the patient. There are also objective indicia of irritation such as petechia, erythemia and edema. Occurrence of such forms of irritation is discussed by Nancy A. Monteiro-Riviere in a paper presented in *Fundamental Applied Technology*, entitled "Altered Epidermal Morphology Secondary to Lidocaine Iontophoresis: In Vivo and In Vitro Studies in Porcaine Skin", Vol. 15, pages 174-185 (1990).

Numerous prior art references attempt to teach iontophoretic devices which attempt to avoid irritation and/or tissue damage. U.S. Pat. No. 4,292,968 to Ellis discloses an apparatus for delivering constant current during ion therapy (iontophoresis) which will abruptly switch to delivering constant voltage when the voltage across the electrodes reaches a predetermined level. U.S. Pat. No. 4,725,263 to McNichols et al. teaches a programmable constant current source transdermal drug delivery system wherein the current level can be adjusted or preset by trimming a circuit board in the apparatus.

U.S. Pat. No. 4,141,359 to Jacobsen et al. teaches an epidermal iontophoresis device which is capable of maintaining a constant current through the epidermal tissue. To prevent excessive voltage build-up and the accompanying dangers of shock and burns, a comparative circuit monitors current flow and voltage across the electrodes and automatically triggers and SCR shut down circuit when impedance readings are outside of predetermined limits.

U.S. Pat. No. 4,211,222 to Tapper teaches an iontophoretic burn protection method. Tapper teaches the use of an electrically conductive porous intervener having a thickness which is large in relation to the thickness of the skin. This intervener is interposed between a first electrode and the skin. Tapper also teaches that pain and tingling due to the passage of electric current can be reduced by increasing the area of the electrode delivering the drug. U.S. Pat. No. 4,164,226 to Tapper teaches iontophoretic burn-protection electrode structures wherein one electrode of an iontophoretic system has a porous material of a thickness in excess of 3 millimeters interposed between the electrode and the skin.

U.S. Pat. No. 4,764,164 to Sasaki teaches an iontophoresis device which includes an electric source including a pulse generator. The device has a circuit for discharging the charges accumulated in the electrodes during each intermission period of therapeutic pulses generated by the pulse generator. Sasaki teaches that the device can be easily applied to the human skin, without causing undesirable irritation in the skin, and especially without causing burns and rubefaction in the skin.

Although the prior art is replete with devices for reducing skin irritation and skin damage, the prior art efforts appear to focus on the device itself. Devices running on lower voltages, devices having intermediate pads between the electrodes and the skin, devices producing pulsating current, and devices having large electrode areas to reduce current concentration all approach the problem from a device perspective. The prior art has not attempted to understand the resistivity of the skin and develop a system that can take advantage of the natural properties of the skin in order to optimize the iontophoretic delivery while minimizing irritation and skin damages.

OBJECTS AND SUMMARY OF THE INVENTION

It is an object of the present invention to provide a device and method for delivering a drug iontophoretically to an animal.

It is another object of the present invention to provide a drug delivery device attachable to a patient for supplying drug to the patient by iontophoresis, and an electronic circuit which operates with the drug delivery device to control the amount of drug and the rate at which the drug is delivered.

It is a further object of the present invention to provide an iontophoretic drug delivery system which minimizes or eliminates undesirable irritation, burning and rubefaction of the skin of the animal to which the system is attached.

It is yet another object of the present invention to provide an electronic circuit which selectively provides a controlled voltage and controlled current to the electrodes of an iontophoretic drug delivery device attachable to a patient.

It is yet a further object of the present invention to provide an electronic circuit which selectively provides a controlled power to the electrodes of an iontophoretic drug delivery device attachable to a patient.

It is still another object of the present invention to provide an iontophoresis system having an electronic circuit which monitors the current and voltage provided to the electrodes of a drug delivery device attachable to the skin of a patient for selectively controlling the amount or rate of current or voltage applied to the electrodes of the drug delivery device.

It is still a further object of the present invention to provide an iontophoretic drug delivery system and method which overcomes the inherent drawbacks of known systems and methods.

In accordance with one form of the present invention, an iontophoretic drug delivery system includes a device having a drug reservoir adapted to be placed in communication with the skin of an animal and an electrolyte reservoir which is adapted to be placed in communication with the skin of the animal. The device includes two electrodes. The first electrode may be mounted at least partially in the drug reservoir, and the second electrode may be mounted at least partially in the electrolyte reservoir.

The drug delivery system includes an electronic circuit coupled to the electrodes of the device having the drug reservoir and the electrolyte reservoir, which circuit selectively provides at least one of a controlled voltage and a controlled current to the electrodes. The circuit includes an adjustable voltage and current generating circuit coupled to the electrodes, a current sensor coupled to one or more of the electrodes for sensing the current provided to the electrodes, and a voltage sensor coupled to one or more of the electrodes for sensing the voltage provided to the electrodes. The current and voltage sensors respectively generate a sensed current feedback signal and a sensed voltage feedback signal, which are representative of the electrode current and voltage sensed by the sensors.

The electronic circuit further includes a comparator circuit for comparing the sensed current feedback signal with a predetermined current threshold signal. A feedback signal selector circuit which is responsive to at least an output signal from the current comparator circuit will generate a feedback signal corresponding to at least one of the sensed current feedback signal and the sensed voltage feedback signal.

The electronic circuit further includes a setpoint selector circuit which is responsive to at least the output signal from the current comparator circuit and, in response thereto, will generate a setpoint signal corresponding to at least one of a voltage limit signal and a desired delivery current signal.

A subtractor circuit will subtract the feedback signal from the setpoint signal and generate an error signal corresponding to the difference between the two. The voltage and current generating circuit is responsive to this error signal and adjusts at least one of the current and voltage provided to the electrodes of the drug delivery device.

These and other objects, features and advantages of this invention will become apparent from the following detailed description of illustrative embodiments thereof, which is to be read in connection with the accompanying drawings.

DETAILED DESCRIPTION OF THE PREFERRED EMBODIMENTS

While this invention is satisfied by embodiments in many different forms, there are shown in the drawings and will herein be described in detail preferred embodiments of the invention with the understanding that the present disclosure is to be considered exemplary of the principles of the invention and is not intended to limit the scope of the invention to the embodiments described. The scope of the invention will be measured by the appended claims and their equivalents.

Adverting to FIGS. 1-7, an operable iontophoretic drug delivery system/device 20 includes a drug reservoir 21 adapted to be attached to the skin of an animal, a first electrode 22 in the drug reservoir, an electrolyte reservoir 23 adapted to be attached to the skin of an animal and a second electrode 25 in the electrolyte reservoir.

For the purposes of the description of the present invention, the term "proximal" or "lower" is meant to refer to the side of the device closest to the skin, whereas the term "distal" or "upper" is meant to refer to the side of the device or element which is furthest from the skin.

For the purpose of description of the present invention and the claims, the term "animal" as used herein shall include all living beings including humans. The term "irritation" as used herein shall mean subjective irritation such as pain and tingling and objective irritation such as petechia, erythemia and edema.

Figure 1:
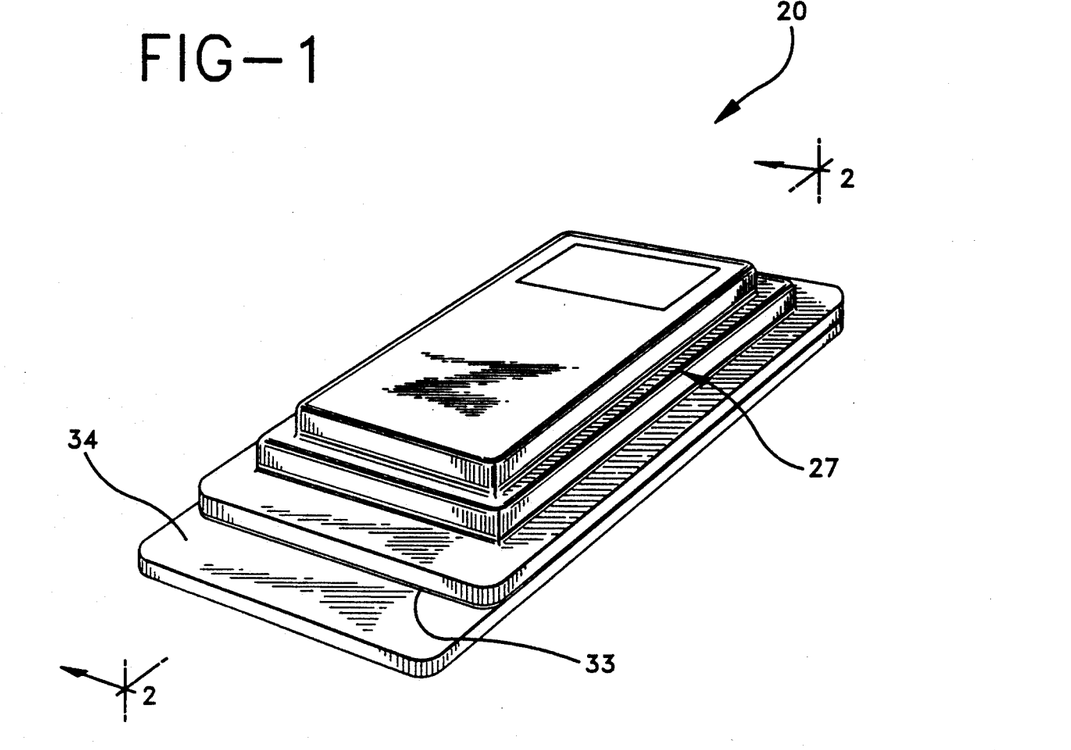
FIG. 1 is a perspective view of an iontophoretic drug delivery system of the present invention.
Figure 2:
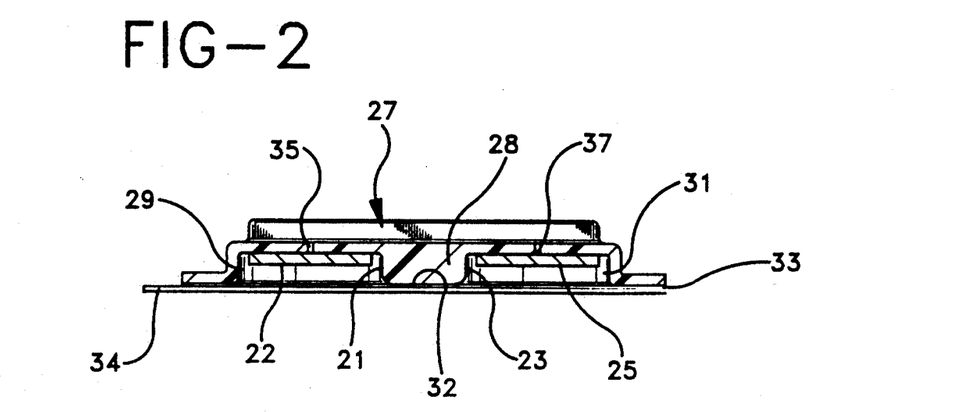
FIG. 2 is a partial cross-sectional view of the drug delivery device of FIG. 1 taken along line 2—2.

In this embodiment, drug reservoir 21 and electrolyte reservoir 23 are part of a common housing 27. First electrode 22 and second electrode 25 are electrically separated by insulating material 28 in the housing. In this embodiment, the entire housing is made of insulating material, such as plastic.

Drug reservoir 21 is capable of holding an ionic compound such as a therapeutic compound, a diagnostic compound and a drug. In many cases, the ionic compounds are ionic liquids, however, the compound may be in the form of a gel or may be contained in the reservoir along with other materials such as porous polymeric structures. For the purpose of the description of this invention, drug reservoir 21 contains a therapeutic liquid 29. This therapeutic liquid does not limit the invention but is intended to be representative of these many possibilities for an ionic compound which can be delivered iontophoretically.

Electrolyte reservoir 23 contains electrolyte solution 31. The electrolyte solution may be in the form of a liquid or a gel, or may be contained in the reservoir along with other materials such as porous polymeric material.

Lower surface 32 of the housing contains an adhesive coating 33 for attaching the housing to the skin of an animal. A removable release sheet 34 is provided to protect the adhesive before time of use and for helping to contain the therapeutic liquid and the electrolyte in the reservoirs before time of use.

The drug delivery device shown in FIGS. 1 and 2 further includes conductors 35 and 37 which are respectively connected to electrodes 2 and 25 and to the electronic circuit of the iontophoresis system of the present invention.

Figure 5:
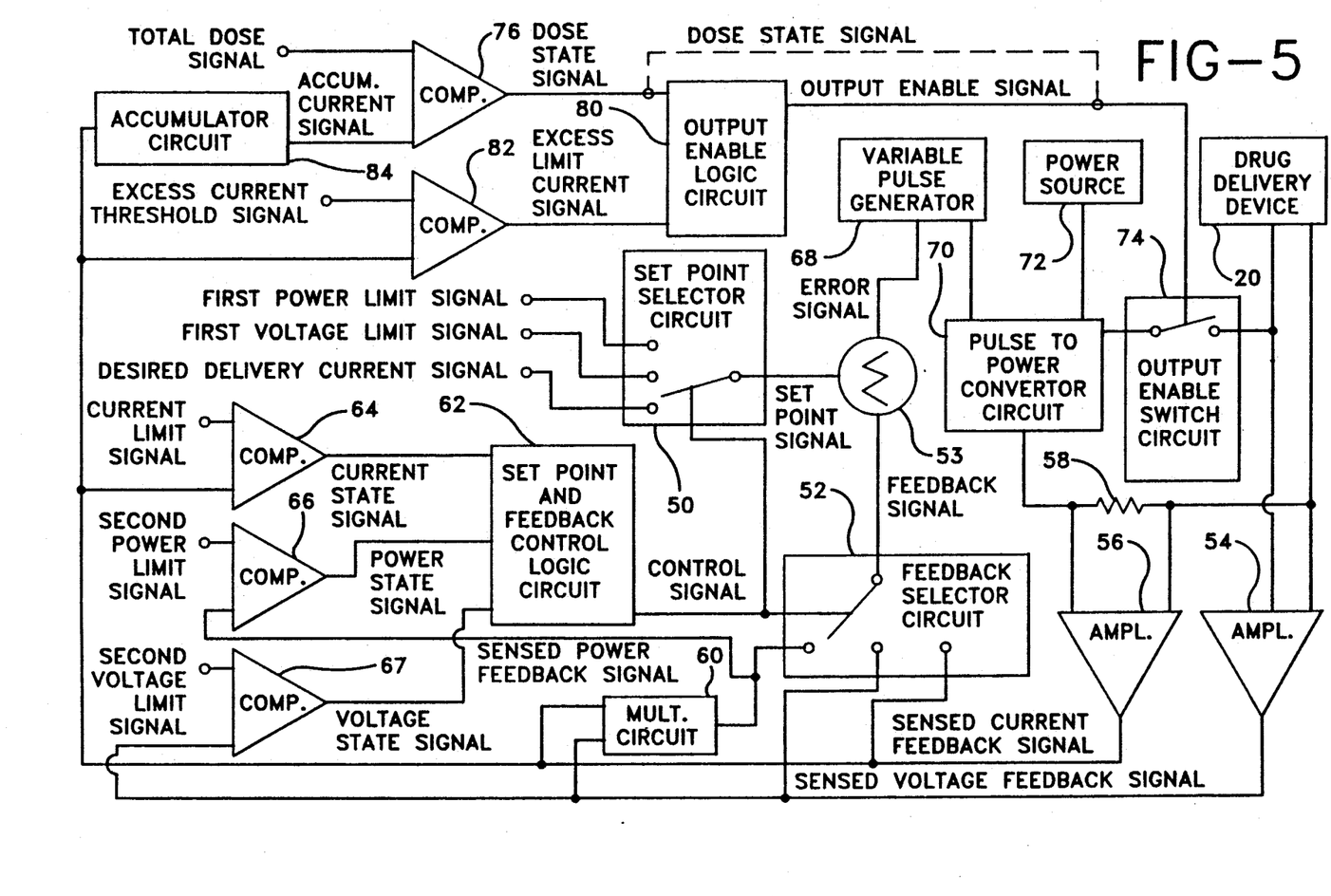
FIG. 5 is a schematic/block diagram view showing a circuit for providing current for iontophoretic delivery of the present invention.

A substantial difference between the iontophoretic drug delivery device of the present invention and the prior art lies in the electronic circuitry, one form of which is shown in FIG. 5. To fully understand the major structural and functional differences between the device of the present invention and the prior art it is important to understand the properties of the skin into which ions are driven by an iontophoretic drug delivery device. The electrical impedance of the skin greatly affects the occurrence of irritation and tissue damage. The electrical impedance of epidermal tissue is highly variable, depending on such factors as location on the body, presence of calluses or dermal abrasions, ambient air conditions such as temperature and humidity, state of hydration which may be caused by perspiration, and the age, sex and race of the individual. It is known that the dose of an ionic substance delivered to an individual is in general proportional to the electric current. In efforts to increase the dose of ionic substance or reduce the time over which a given dose may be administered, the electric current is often raised to a level which results in skin irritation and skin damage including burns. For example, Jacobsen et al. in U.S. Pat. No. 4,141,359 cite native values of skin impedance of 10,000 to 50,000 ohms. If a modest current of 3 milliamperes is caused to flow through skin with an average value of 30,000 ohms, the required voltage by Ohms' Law would be 30,000 ohms times 0.003 amperes or 90 volts. Such a voltage is widely known to be capable of causing irreversible skin breakdown, which is believed to provide low resistance paths, and hence paths where high levels of energy are dissipated in the skin. This high level of energy is believed to cause burns.

During iontophoresis episodes, the impedance of skin through which ions are transferred is initially at a high value, and then steadily decreases. The instant invention provides a device and a method for effective iontophoretic delivery while minimizing irritation and burns by accommodating the highly variable nature of skin impedance.

Figure 3:
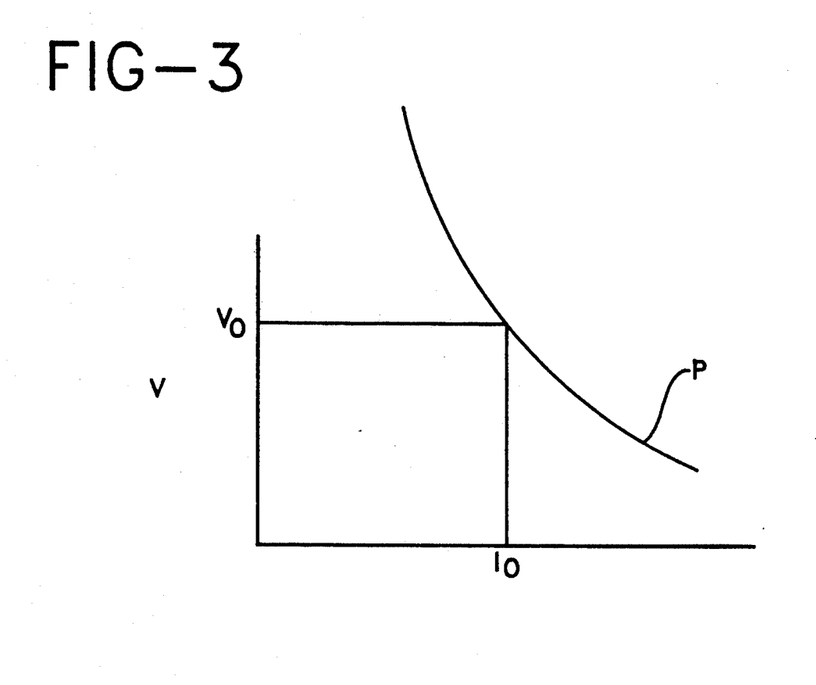
FIG. 3 and FIG. 4 are graphs illustrating voltage, current and power which demonstrate the operation of the present invention.
Figure 6:
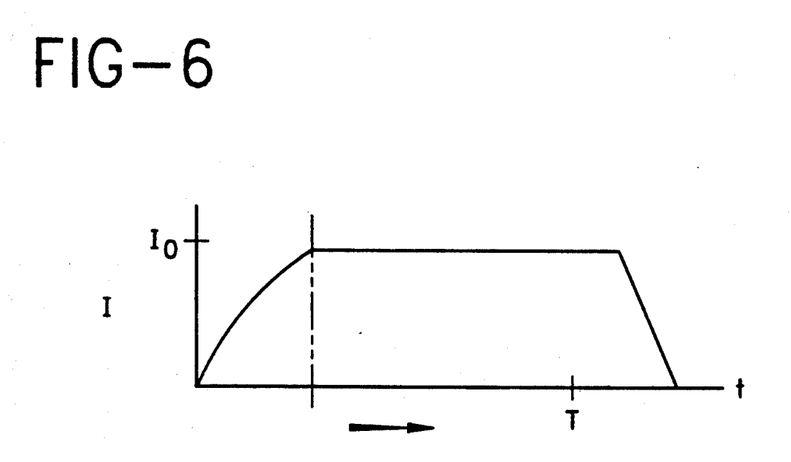
FIG. 6 is a graph illustrating a profile of current with respect to time for iontophoretic delivery of the present invention.
Figure 7:
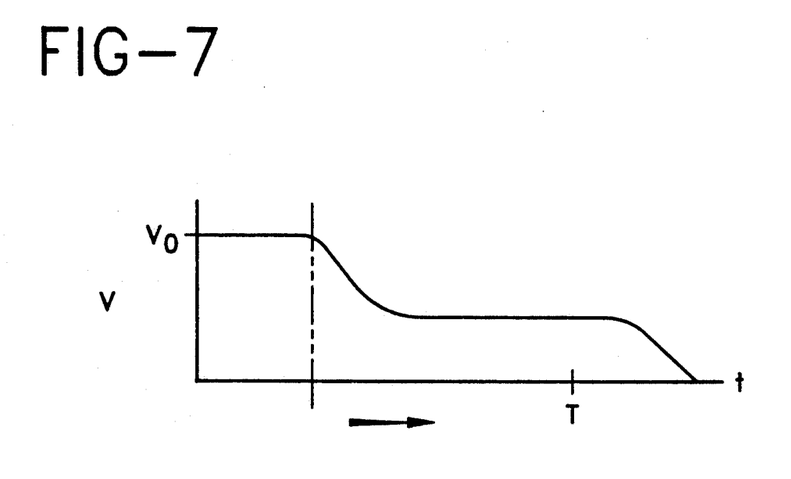
FIG. 7 is a graph illustrating voltage with respect to time for iontophoretic delivery using the present invention.

The method and the device of the instant invention work as follows. An iontophoretic delivery device such as device 20 is attached to the skin of an animal. The attachment can be accomplished by removing the backing sheet and pressing the device against the skin. Next, electrical power is caused to flow between the electrodes at a constant voltage $V_o$ as illustrated in FIGS. 3 and 7. $V_o$ is of a sufficiently low magnitude not to cause irritation to the skin. Because the initial high impedance of skin, the current is at a low value during this time as illustrated in FIG. 6. Because current is flowing, the skin impedance begins to fall allowing more current to flow. This in turn causes the skin impedance to decrease further, which permits more current to flow, and so on as illustrated in FIG. 6. At time T in FIG. 6 the current reaches the pre-selected value of $I_o$. When $I_o$ is reached, the electronic circuit, supplying a controlled voltage $V_o$ to the electrodes, as will be explained in more detail hereinafter, switches modes and becomes a constant current source (see FIGS. 6 and 7). FIG. 6 illustrates the rise of current to $I_o$ at which time current becomes constant at $I_o$. When $I_o$ is reached, and the system delivers constant current $I_o$, the voltage begins falling. This falling off of voltage from the $V_o$ value is due to the decreasing resistance of the skin. The instant invention functions such that the voltage is prevented from rising to a level which can cause irreversible skin breakdown which leads to burns. At the same time, the desirable constant current capability is provided once the switchover to $I_o$ is achieved.

Accordingly, the instant invention may be used by attaching an iontophoretic drug delivery device to the skin, as described hereinabove, and to at least initially impress a constant voltage across the electrodes of the device. The current flowing through the electrodes is monitored while the constant voltage is applied. The electronic circuit senses when the monitored current reaches a predetermined current, such as $I_o$, and switches from supplying a constant voltage to the electrodes to supplying a constant current, $I_o$. This current continues to flow between the electrodes, at a constant predetermined rate, until the therapy regimen is completed.

It is known that there is a relationship between the current delivered to the electrodes and the quantity of ions transferred through the skin. Accordingly, the amount of current with respect to time can be measured to determine the amount of drug transferred through the skin. When using the method of the instant invention, the user can monitor the total current (overtime) flowing between the electrodes and terminate power to the electrodes when the total amount of current, corresponding to the delivery of the desired amount of ionic compound into the skin, has been achieved.

Figure 4:
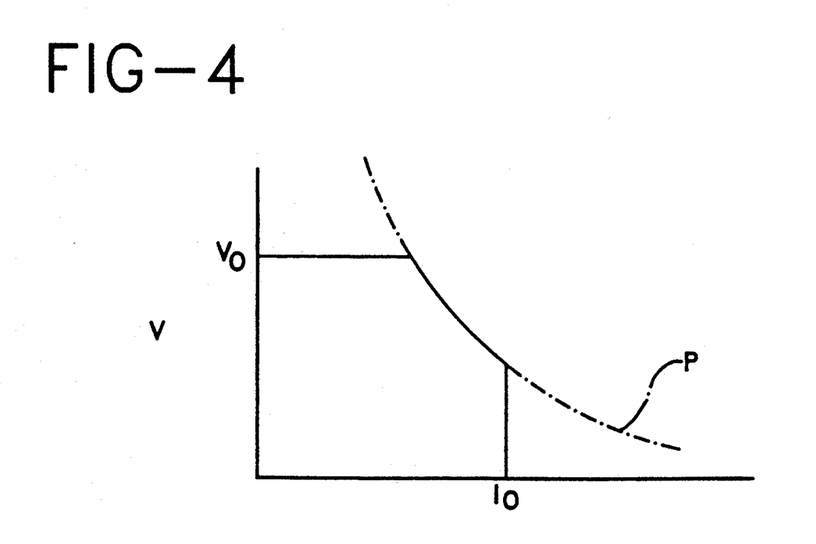

It is known that high values of voltage and current will cause irritation and skin burning. Therefore, the present invention also provides a method and a device for limiting the amount of power that can be transmitted through the electrode system. As illustrated in FIG. 3, in some instances, the desirable power limit shown by the current designated $P_o$ is beyond the desirable values for $V_o$ and $I_o$. However, in other circumstances if the iontophoretic delivery was carried out at $V_o$ until the value of $I_o$ was reached, irritation may be caused to the skin. Accordingly, as best illustrated in FIG. 4, the present method and device incorporates safeguards so that in carrying out the transition from constant voltage to constant current, a predetermined constant power P1 is not exceeded. In carrying out the method of the instant invention, the power supplied to the electrodes is monitored throughout the delivery of current at constant voltage $V_o$. If the power reaches a predetermined Value, the voltage is lowered along the constant power curve P1 until the desired $I_o$ value is reached, as illustrated in FIG. 4. As will be explained in greater detail, the instant invention includes circuitry to implement the transition between constant voltage and constant current along a constant power curve.

One form of the electronic circuit for providing a controlled voltage, current or power to the electrodes of the drug delivery device 20 is shown in FIG. 5. The electronic circuit includes a set point selector circuit 50. Set point selector circuit 50 functions as an electronic, single pole, triple throw switch. The set point selector circuit includes: three inputs which are the poles of the switch; an output, which is effectively connected to the wiper of the switch; and a control input, which effectively controls the position of the wiper and its connection to one of the poles of the circuit.

Three predetermined voltage level signals are provided on the inputs of the set point selector circuit 50. A first voltage level is provided on a first input and represents a first power limit signal which is the maximum amount of power which is desired to be supplied to the electrodes of the drug delivery device 20. A second predetermined voltage level is provided to a second input of the set point selector circuit 50 and represents a first voltage limit signal, that is, the maximum voltage which is to be supplied to the electrodes of device 20. A third predetermined voltage level is provided to the third input of the set point selector circuit 50 and represents the desired delivery current, that is, the constant o current which is desired to flow between the electrodes of device 20. One of these predetermined voltage level signals on passed through the selector circuit to the output in response to a control signal provided to the control input of the set point selector circuit. Accordingly, the set point selector circuit 50 provides a set point signal on its output which is, effectively, a predetermined voltage level.

The electronic circuit further includes a feedback selector circuit 52. Feedback selector circuit 52 is similar in many respects to the set point selector circuit 50. It functions electronically as a single pole, triple throw switch, having three separate inputs which are the poles of the switch, a single output (connected effectively to the wiper of the switch), and a control input which effectively controls the position of the wiper and the connection between the output of the feedback selector circuit and one of its three inputs.

Three voltage levels are provided on the inputs of feedback selector circuit 52. The first voltage level is provided to the first input and is a sensed current feedback signal. The second voltage level is provided to the second input of the feedback selector circuit 52 and is a sensed voltage feedback signal. The third voltage level is provided to the third input and is a sensed power feedback signal. As will be explained in greater detail, each of these signals results from monitoring and measuring the current and voltage provided to the drug delivery o device 20 by the electronic circuit. The output of the feedback selector circuit 52 provides a feedback signal which, as will be explained, is compared to the set point signal in a summer or subtractor circuit 53.

The voltage and current supplied to the drug delivery device 20 are monitored by differential amplifiers 54 and 56. The first differential amplifier 54 has each of its two inputs coupled to one of the electrodes of the transdermal drug delivery device 20. The output of the amplifier 54 provides a sensed voltage feedback signal, as described previously, which varies proportionally to the voltage supplied across the electrodes of device 20.

The second differential amplifier 56 has its two inputs connected across a current sense resistor 58 which is connected in series with one of the electrodes of device 20. The current flowing through the electrodes will also flow through current sense resistor 58, which is a fixed resistor of relatively low value, and will cause a voltage drop across the resistor, which is sensed by second differential amplifier 56. The output of the second differential amplifier 56 provides a sensed current feedback signal, as described previously. The sensed voltage and current feedback signals are provided to the respective inputs of feedback selector circuit 52.

The electronic circuit of the iontophoresis system further includes a multiplication circuit 60. Multiplication circuit 60 includes two inputs on which are provided the sensed current feedback signal and the sensed voltage feedback signal. The multiplication circuit 60 multiplies the two feedback signals and provides a sensed power feedback signal on its output. The sensed power feedback signal is provided to one of the inputs of the feedback selector circuit 52, as described previously.

Set point selector circuit 50 and feedback selector circuit 52 are controlled by a set point and feedback control logic circuit 62. Set point and feedback control logic circuit 62 generates a control signal which is provided to the control inputs of each of the set point selector circuit 50 and feedback selector circuit 52. The set point and feedback control logic circuit 62 may, in one form, be a read only memory (ROM), having preferably three inputs. On one input is provided a current state signal, and on another input is provided a power state signal, and on a third input is provided a voltage state signal. Each of the current state signal, and voltage state signal and power state signal is preferably a logic signal, and the control signal generated by the set point and feedback control logic circuit 62 is also preferably a logic signal.

The electronic circuit of the iontophoresis system further includes a first and second comparator 64 and 66, and in a preferred form of the invention, a third comparator 67. First comparator 64 generates the current state signal on its output, and second comparator 66 generates the power state signal on its output. Third comparator 67 generates the voltage state signal on its output. First comparator 64 is provided with a current limit signal, which may be in the form of a selectable DC voltage, on one of its inputs. The current limit signal may be equal to the desired delivery current signal provided to the set point selector circuit 50. The other input of the first comparator 64 is provided with the sensed current feedback signal.

Similarly, second comparator 66 is provided with a second power limit signal, which may be in the form of a preselected voltage level, on one of its inputs. The second power limit signal may be equal to the first power limit signal provided to the set point selector circuit 50. The other input of the second comparator 66 is provided with the sensed power feedback signal generated by multiplier circuit 60.

The third comparator 67 is provided with a second voltage limit signal, which may be in the form of a preselected voltage level, on one of its outputs. The second voltage limit signal may be equal to the first voltage limit signal provided to the set point selector circuit 50. The other input of the third comparator 67 is provided with the sensed voltage feedback signal.

The current state signal will be at one logic level when the current limit signal is greater than the sensed current feedback signal provided to the first comparator 64, and will be in a second logic state when the current limit signal is less than or equal to the sensed current feedback signal. Similarly, the power state signal will be in one logic state when the second power limit signal is greater than the sensed power feedback signal provided to the second comparator 66, and will be in a different state when the power limit signal is less than or equal to the sensed power feedback signal. The voltage state signal will be in one logic state when the second voltage limit signal is greater than the sensed voltage feedback signal provided to the third comparator 67, and will be in a different state when the voltage limit signal is less than or equal to the sensed voltage feedback signal.

Set point and feedback control logic circuit 62 is preprogrammed to provide different control signals in response to the different conditions of the current state signal and the second power state signal and, if the third comparator 67 is included in the second voltage limit signal. If the sensed current feedback signal and the sensed power feedback signal are respectively below the current limit signal and the second power limit signal provided to the first and second comparators 64 and 66, set point and feedback control logic circuit 62 will generate a control signal which will cause set point selector circuit 50 and feedback selector circuit 52 to provide respectively a set point signal and feedback signal which are equal or correspond to the first voltage limit signal (provided to the set point selector circuit 50) and the sensed voltage feedback signal (provided to the feedback selector circuit 52). If the sensed current feedback signal is below the current limit signal provided to first comparator 64, and the sensed power feedback signal is greater than or equal to the second power limit signal provided to second comparator 66, set point and feedback control logic circuit 62 will provide a control signal which will cause set point selector circuit 50 and feedback selector circuit 52 to provide respectively a set point signal and a feedback signal which are equal or correspond to the first power limit signal provided to the set point selector circuit 50 and the sensed power feedback signal provided to feedback selector circuit 52.

If the sensed current feedback signal is greater than or equal to the current limit signal provided to first comparator 64, and the sensed power feedback signal is less than the second power limit signal provided to the second comparator 66, the set point and feedback control logic circuit 62 will provide a control signal to the set point selector circuit 50 and the feedback selector circuit 52 such that the set point selector circuit and the feedback selector circuit will respectively generate a set point signal and feedback signal which are equal or correspond to the desired delivery current signal provided to the set point selector circuit 50 and the sensed current feedback signal provided to feedback selector circuit 52. If the sensed current feedback signal is greater than or equal to the current limit signal provided to the first comparator 64, and the sensed power feedback signal is greater than or equal to the power limit signal provided to second comparator 66, set point and feedback control logic circuit 62 will generate a control signal which will cause the set point selector circuit and the feedback selector circuit to generate respectively a set point signal and a feedback signal which are equal or correspond to the first power limit signal provided to set point selector circuit 50 and the sensed power feedback signal provided to feedback selector circuit 52.

It is possible that the impedance of the patient's skin may increase while the transdermal delivery system is operating in the constant current mode. This will cause the voltage delivered to the patient to increase, possibly causing discomfort, or even injury if a power limit is not used. Under such circumstances, it may be desirable for the circuit to switch back into a controlled, constant voltage mode. The third comparator 67 may be included for such a purpose. Thus, if the sensed voltage feedback signal equals or exceeds the second voltage limit provided to the third comparator 67, the set point and feedback control logic circuit 62 will provide a control signal to the set point selector circuit 50 and the feedback selector circuit 52 such that the set point selector circuit and the feedback selector circuit will respectively generate a set point signal and feedback signal which are equal or correspond to the first voltage limit signal (provided to the set point selector circuit 50) and the sensed voltage feedback signal (provided to the feedback selector circuit 52).

Of course, it should be realized that the set point and feedback control circuit 62 will cause the delivery system to go into a controlled constant power mode if the sensed power feedback signal equals or exceeds the second power limit signal provided to the second comparator 66. This will occur whether or not the current limit signal or the second voltage limit signal is exceeded.

The following table illustrates the mode which the circuit will be in in response to whether the sensed current, voltage and power feedback signals are above or below their respective threshold limits provided to comparators 64, 66 and 67.

TABLE 1

| C | V | P | MODE |
|---|---|---|------|
| Below Limit | Below Limit | Below Limit | Voltage |
| Above or Equal to Limit | Below Limit | Below Limit | Current |
| Below Limit | Above or Equal to Limit | Below Limit | Voltage |
| Above or Equal to Limit | Above or Equal to Limit | Below Limit | Voltage |
| X | X | Above or Equal to Limit | Power |

C = sensed current feedback signal
V = sensed voltage feedback signal
P = sensed power feedback signal
X = "don't care" condition It should be noted that an alternative form of the invention would omit the power mode and its related structure such as comparator 66, multiplication circuit 60 and the first and second power limit signals. The circuit would include the structure described previously, including comparators 64 and 67, which would allow the circuit to switch between a controlled, constant current mode and a controlled constant voltage mode.

As mentioned previously, the set point signal and feedback signal are provided to a summer or subtractor circuit 53. Summer or subtractor circuit 53 will subtract the feedback signal from the set point signal and provide an error signal on its output, which error signal corresponds to the difference in voltage levels between the set point signal and the feedback signal.

The error signal from the summer circuit 53 is, in one form of the invention, provided to the input of a variable pulse generator 68, such as a voltage controlled oscillator (VCO). Variable pulse generator 68 provided a pulsed output signal which varies in either frequency or duty cycle proportionally to the magnitude of the error signal generated by summer circuit 53.

The electronic circuit of the iontophoresis system further includes a pulse to power converter circuit 70. Pulse to power converter circuit 70 includes an input to which is provided the output signal from variable pulse generator 68, and a pair of outputs across which is a controlled voltage which is generated by the pulse to power converter circuit from a power source 72 connected to another input of the converter circuit 70. The output voltage generated by pulse to power converter circuit 70 across its outputs will vary in accordance with the frequency or duty cycle of the pulsed output signal from the pulse generator 68 and, in turn, the voltage level of the error signal generated by summer circuit 53.

Figure 5A:
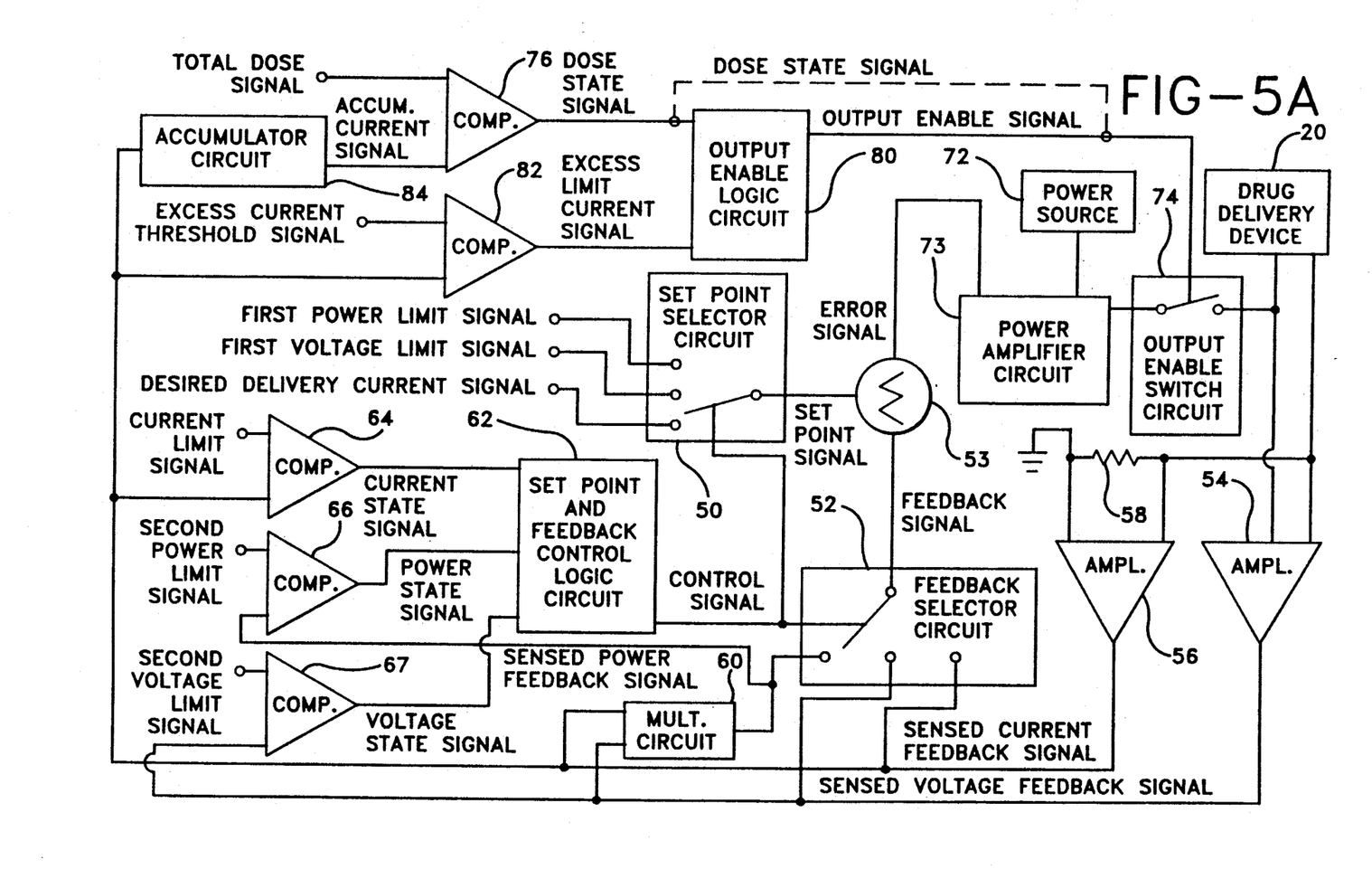
FIG. 5A is a block diagram of a first alternative embodiment of the electronic circuit of the iontophoresis system formed in accordance with the present invention.

An alternative embodiment of the system circuit is shown in FIG. 5A. The pulse generator 68 and pulse to power converter circuit 70 may be replaced with a power amplifier circuit 73. The power amplifier circuit 73 includes an input which receives the error signal from summer circuit 53, and generates an output voltage which varies in response to the error signal. The output voltage is provided to the drug delivery device 20 in a manner similar to that which is described in relation to the embodiment of FIG. 5.

The portion of the electron circuit of the iontophoresis system thus described provides a selectable, controlled constant voltage, constant current or constant power to the electrodes of the transdermal drug delivery device 20, as described previously, through feedback. When the iontophoresis system is initially applied to the patient, the current sensed by the circuit flowing through the electrodes will be at a relatively low level, that is, less than the $I_o$ threshold, because of the relatively high resistance of the patient's tissue. Under such conditions, the electronic circuit will be in a constant voltage mode so as to provide a constant voltage to transdermal delivery device 20. The sensed voltage feedback and the voltage limit signal will, effectively, be compared in summer circuit 53, and any differences between the two will be adjusted for by pulse to power converter circuit 70 (or power amplifier circuit 73, as shown in FIG. 5A).

When the sensed current feedback signal rises to the level of the current limit signal, because of the decrease in the resistance to the patient's tissue, the electronic circuit will switch into a constant current mode. The control signal generated by set point and feedback control logic circuit 62 will cause the delivery current signal and the sensed current feedback signal to be provided to summer or subtractor circuit 53 in order to control variable pulse generator 68 driving pulse to power converter circuit 70. Any differences between the desired delivery current signal and the sensed current feedback signal will be adjusted for by pulse to power converter circuit 70 and the feedback loop of the electronic circuit.

If, either in the constant voltage mode or the constant current mode, the sensed power feedback signal equals or exceeds the second power limit signal, set point and feedback control logic circuit 62 will generate a control signal such that the electronic circuit will go into a constant power mode. The control signal will cause the first power limit signal and the sensed power feedback signal to be provided to the inputs of summer or subtractor circuit 53, and any differences between the two will be adjusted for by pulse to power converter circuit 70 (or power amplifier circuit 73) and the feedback loop of the electronic circuit.

The iontophoresis system of the present invention indirectly monitors and measures the total quantity of the drug provided transdermally to the patient, and will stop delivery when a selectable, predetermined total dosage level is reached. More specifically, the electronic circuit includes an output enable switch circuit 74 in the form of an electronic, single pole, single throw switch, which is connected between one output of the pulse to power converter circuit 70 (or amplifier 73 in the embodiment of FIG. 5A) and one of the electrodes of the drug delivery device 20. The position of the "wiper" of output enable switch circuit 74 is controlled by a dose state signal provided to the control input of the switch. Preferably, the dose state signal is a logic signal which is generated by a fourth comparator 76 on its output, and is provided to switch circuit 74 partially along dashed line 78, which bypasses an output enable logic circuit 80 of an alternative form of the present invention, as will be described in greater detail.

Fourth comparator 76 includes at least two inputs. A total dosage signal, which may be in the form of a preselected voltage level, is provided on one input, and an accumulated current signal, which may also be in the form of a variable voltage level, is provided to the other input of the fourth comparator 76.

The electronic circuit further includes an accumulator circuit 82. The accumulator circuit 82 has an input on which is provided the sensed current feedback signal and an output on which is provided the accumulated current signal. Accumulator circuit 82 effectively integrates and accumulates the sensed current feedback signal over time. It may be in the form of a circuit in which the sensed current feedback signal is converted from a voltage to a current which accumulates charge on a capacitor, the resulting voltage across the capacitor increasing in proportion to the current flowing into it. The voltage across the capacitor may be used in generating the accumulated current signal.

The accumulated current signal, which is in the form of a variable voltage level, is proportional to the current flowing through the electrodes of the transdermal drug delivery device 20, which current, in turn, is representative of the total drug dose administered to the patient. If the accumulated current signal is below the total dose signal, the dose state signal generated by fourth comparator 76 will be in one state and will cause output enable switch circuit 74 to maintain the connection between pulse to power converter circuit 70 (or amplifier 73) and one of the electrodes of delivery device 20. If the accumulated current signal equals or exceeds the total dose signal, the dose state signal will be in another state which will cause the output enable switch circuit 74 to open, disconnecting the pulse to power converter circuit 70 (or amplifier 73) from drug delivery device 20. Accordingly, the electronic circuit of the iontophoresis system will automatically disconnect power to drug delivery device 20 when the proper drug dosage has been administered to the patient.

In a preferred form of the present invention, the electronic circuit may further include an over-current shut down comparator circuit. This circuit disables the output of the pulse to power converter circuit 70 (or amplifier 73) in the event that the sensed current feedback signal exceeds a predetermined level, which preferably corresponds to 1.5 times the current delivered to the electrodes of drug delivery device 20.

More specifically, the over-current shut down comparator circuit includes an output enable logic circuit 80, which may be in the form of a ROM, which is interposed between the output of the fourth comparator 76 and the control input of output enable switch circuit 74. The output enable logic circuit 80 provides an output enable signal to output enable switch circuit 74 to control the position of the switch circuit in much the same way as the dose state signal from fourth comparator 76 did in the previous embodiment.

The dose state signal from fourth comparator 76, in this embodiment, is provided to one input of output enable logic circuit 80. An excess current limit signal, which may be in the form of a logic signal, is provided to another output of output enable logic circuit 80. The excess current limit signal is generated by a fifth comparator 82 on its output.

Fifth comparator 82 includes two inputs. One input is provided with an excess current threshold signal, which may be in the form of a pre-selected voltage level which may be equal to 1.5 times the voltage level of the desired delivery current signal. The second input is provided with the sensed current feedback signal.

The output enable logic circuit 80 will control the state of output enable switch circuit 74 in response to whether a total dose has been administered to the patient or whether the instantaneous, sensed current feedback signal exceeds the excess current threshold signal. More specifically, if the accumulated current signal is less than the total dose signal, the output enable signal generated by output enable logic circuit 80 will be such as to cause output enable switch circuit 74 to maintain a connection between the pulse to power converter circuit 70 (or amplifier circuit 73) and drug delivery device 20.

Irrespective of whether the total dose has been administered to the patient, if the sensed current feedback signal equals or exceeds the excess current threshold signal, fifth comparator 82 will provide an output signal to output enable logic circuit 80 which, in turn, will cause the output enable signal to open the output enable switch circuit 74, thereby disconnecting the pulse to power converter circuit 70 (or amplifier 73) from the drug delivery device 20. If, of course, the excess current threshold signal has not been exceeded or reached by the sensed current feedback signal and the total dose signal is greater than the accumulated current signal, the output enable logic circuit 80 will cause the output enable switch circuit 74 to maintain a connection between the pulse to power converter circuit 70 (or amplifier 73) and the drug delivery device 20. Thus, the electronic circuit of the iontophoresis system will automatically disconnect power from drug delivery device 20 if either the total dose has been administered to the patient or an excess current condition has been detected.

Figure 5B:
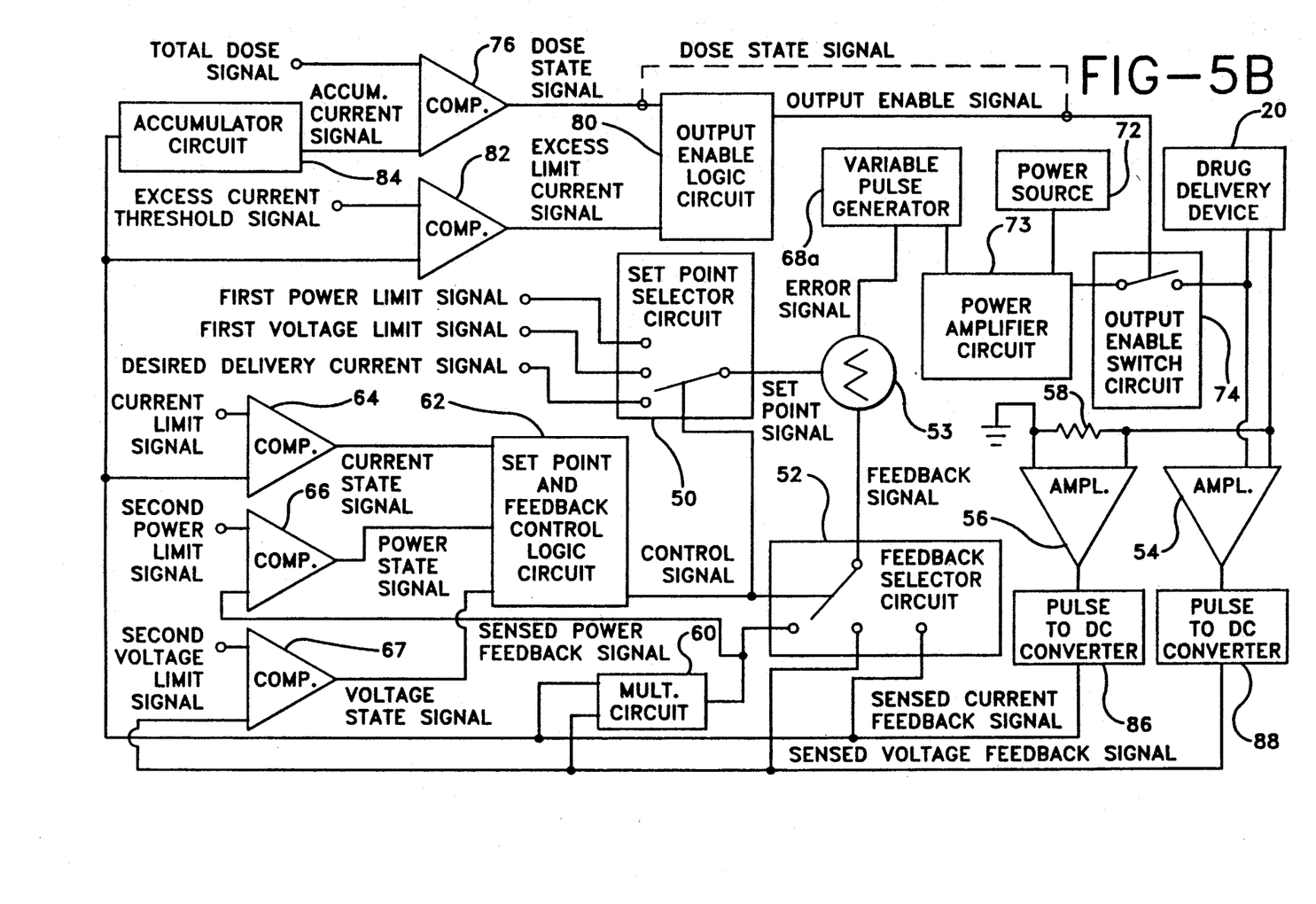
FIG. 5B is a schematic/block diagram of a second alternative embodiment of the electronic circuit of the iontophoresis system formed in accordance with the present invention.

The circuits shown in FIG. 5 and 5A and described previously provide a controlled, constant direct current or voltage to the transdermal drug delivery device 20. However, it is envisioned to be within the scope of the invention to include a circuit which provides a controlled pulsed voltage or current to delivery device 20. Such a current is shown in FIG. 5B.

The pulse version of the circuit would include a variable pulse generator 68a, or the combination of a pulse generator 68a and power amplifier circuit 73, as shown in FIG. 5A, in lieu of the pulse to power converter circuit 70. The variable pulse generator 68a provides a pulsed output signal which varies in either frequency or duty cycle, or in amplitude at a constant frequency or duty cycle, proportionally to the magnitude at a constant frequency or duty cycle, proportionally to the magnitude of the error signal generated by the summer circuit 53.

First and second pulse to DC converter circuits 86,88 are respectively interposed in the circuit between amplifiers 56 and 54 and the feedback selector circuit 52. The pulse to DC converter circuits 86,88 are essentially averaging circuits or integrators which receive the output signals from amplifiers 56,54 and provide on their output a sensed current feedback signal and sensed voltage feedback signal which correspond to the average value of the pulsed current and pulsed voltage provided to the delivery device 20 and monitored by amplifiers 56 and 54. Thus, the sensed current and voltage feedback signals are DC signals which vary in magnitude proportionally with the pulsed current and voltage provided to delivery device 20 by variable pulse generator 68a and a power amplifier circuit 73. The remainder of the pulse version of the iontophoresis system circuit has the same structure and functions in the same way as the circuits described previously and shown in FIGS. 5 and 5A.

What is claimed is:

1. An operable iontophoretic drug delivery system comprising:
    a drug reservoir adapted to be attached to the skin of an animal;
    a first electrode in said drug reservoir;
    an electrolyte reservoir adapted to be placed in communication with the skin of an animal;
    a second electrode in said electrolyte reservoir;
    circuit means for providing electrical communication between said first and second electrodes, said circuit means including means for connection to a source of electrical power;
    means for providing substantially constant voltage between said electrodes, in said circuit means, including means for monitoring current through said first electrode;
    means for providing substantially constant current to said first electrode, in said circuit means; and
    switching means, in said circuit means, for switching from said means for providing constant voltage to said means for providing constant current when said current monitored by said monitoring means reaches a predetermined value.

2. The operable iontophoresis drug delivery system of claim 1 further including means for measuring the current passing through said first electrode and for accumulating the total current passing through said first electrode.

3. The operable iontophoresis drug delivery system of claim 2, further including means for terminating power to said first electrode when accumulated total current reaches a predetermined value.

4. The operable iontophoresis drug delivery system of claim 1, wherein said drug reservoir contains an ionic compound selected from the group consisting of therapeutic compounds, diagnostic compounds and drugs.

5. The operable iontophoresis drug delivery system of claim 1, wherein said first electrode includes a conductive element selected from the group consisting of silver, silver/silver chloride, gold, copper, molybdenum and lead.

6. The operable iontophoresis drug delivery system of claim 1, wherein said drug reservoir and said electrolyte reservoir are part of a common housing.

7. The operable iontophoresis drug delivery system of claim 6, wherein said housing is made of plastic.

8. The operable iontophoresis drug delivery system of claim 6, wherein said housing includes a removable release sheet covering both reservoirs and a portion of said housing adapted to contact the skin of an animal.

9. The operable iontophoresis drug delivery system of claim 1, wherein said drug reservoir and said electrolyte reservoir include an adhesive coated surface for attachment to the skin of an animal.

10. An operable iontophoretic drug delivery system comprising:
  a drug reservoir adapted to be attached to the skin of an animal;
  a first electrode in said drug reservoir;
  an electrolyte reservoir adapted to be placed in communication with the skin of an animal;
  a second electrode in said electrolyte reservoir;
  circuit means for providing electrical communication between said first and second electrodes, said circuit means including means for connection to a source of electrical power;
  means for providing substantially constant voltage between said electrodes, in said circuit means, including at least one of means for monitoring current through said first electrode and means for monitoring voltage between the first and second electrodes;
  means for providing substantially constant current to said first electrode, in said circuit means;
  switching means, in said circuit means, for switching between said means for providing constant voltage and said means for providing constant current when at least one of the monitored current and monitored voltage equals a predetermined value; and
  power limiting means in said switching means for causing a transition from one constant voltage and constant current to a constant power provided to the first and second electrodes if a predetermined power, monitored by said power limiting means, is reached.

11. An operable iontophoretic drug delivery system comprising:
  a drug reservoir adapted to be attached to the skin of an animal;
  a first electrode in said drug reservoir;
  an electrolyte reservoir adapted to be placed in communication with the skin of an animal;
  a second electrode in said electrolyte reservoir;
  circuit means for providing electrical communication between said first and second electrodes, said circuit means including means for connection to a source of electrical power;
  means for providing substantially constant voltage between said electrodes, in said circuit means, including at least one of means for monitoring current through said first electrode and means for monitoring voltage between the first and second electrodes;
  means for providing substantially constant current to said first electrode, in said circuit means;
  switching means, in said circuit means, for switching between said means for providing constant voltage and said means for providing constant current when at least one of the monitored current and monitored voltage equals a predetermined value; and
  power limiting means, in said switching means, for causing a transition from one constant voltage and constant current to a constant power provided to the first and second electrodes if a predetermined power is reached.

12. The operable iontophoresis drug delivery system of claim further including means for measuring the current passing through said first electrode and for accumulating the total current passing through said first electrode.

13. The operable iontophoresis drug delivery system of claim 11, wherein said drug reservoir contains an ionic compound selected from the group consisting of therapeutic compounds, diagnostic compounds and drugs.

14. A circuit for connecting a pair of electrodes of an iontophoretic drug delivery system comprising:
  means for connecting said circuit to a source of power;
  means for providing substantially constant voltage between said electrodes;
  means for providing a substantially constant current to one of said electrodes;
  means for monitoring current through one of said electrodes;
  means for switching from said means for providing constant voltage to said means for supplying constant current when said current monitored by said monitoring means reaches a predetermined value.

15. A circuit for connecting to a pair of electrodes of an iontophoretic drug delivery system comprising:
  means for connecting said circuit to a source of power;
  means for providing substantially constant voltage between said electrodes;
  means for providing a substantially constant current to one of said electrodes;
  at least one of means for monitoring current through one of said electrodes and means for monitoring voltage between the electrodes;
  means for switching between said means for providing constant voltage and said means for providing constant current when at least one of the monitored current and the monitored voltage equals a predetermined value; and
  power limiting means in said switching means for causing a transition from one of said constant voltage and constant current to a constant power provided to the electrodes if a predetermined power between said electrodes is reached.

16. A method for iontophoretic drug delivery through the skin of an animal using an iontophoretic drug delivery device having an ionic compound containing reservoir, a first electrode in said ionic compound containing reservoir, an electrolyte containing reservoir, and a second electrode in said electrolyte containing reservoir comprising the steps of:
  (a) attaching said iontophoretic drug delivery device to the skin of an animal;
  (b) causing electrical power to flow between said electrodes at a constant predetermined voltage;
  (c) monitoring the current while said power is being delivered at constant voltage;
  (d) when said monitored current reaches a predetermined current causing the electrical power between said electrodes to change from constant voltage to constant current at said predetermined current; and
  (e) continuing to cause electrical power to flow between said electrodes at a constant predetermined current.

17. The method for iontophoretic drug delivery of claim 16, having additional steps comprising:
  (f) monitoring and accumulating the total current passing between said electrodes; and
  (g) terminating electrical power provided to said electrodes when the accumulated total amount of current, corresponding to the delivery of the desired amount of ionic compound into the skin of the animal, has been reached.

18. A method for iontophoretic drug delivery through the skin of an animal using an iontophoretic drug delivery device having an ionic compound containing reservoir, a first electrode in said ionic compound containing reservoir, an electrolyte containing reservoir, and a second electrode in said electrolyte containing reservoir comprising the steps of:
   (a) attaching said iontophoretic drug delivery device to the skin of an animal;
   (b) causing electrical power to flow between said electrodes at at least one of a constant predetermined voltage and a constant predetermined current;
   (c) at least one of monitoring the current to one of the first and second electrodes while said power is being delivered at constant voltage and monitoring the voltage between the first and second electrodes while said power is being delivered at a constant current;
   (d) when at least one of the monitored current and monitored voltage equals a predetermined value, causing the electrical power between the first and second electrodes to change between a constant voltage and a constant current;
   (e) monitoring power between said electrodes; and
   (f) if the monitored power reaches a predetermined value, causing the power to the electrodes to change from one of constant voltage and constant current to a constant power provided to the electrodes.

19. In combination:
   a drug delivery device attachable to a patient for supplying a drug to the patient by iontophoresis, the drug delivery device including a pair of electrodes; and
   an electronic circuit coupled to the electrodes of the drug delivery device and selectively providing at least one of a controlled voltage and a controlled current to the electrodes, the electronic circuit comprising:
   adjustable voltage and current generating means coupled to the electrodes of the drug delivery device and providing one of a selectively adjustable current and voltage to the electrodes;
   means for sensing the current provided to the electrodes of the drug delivery device, the current sensing means generating a sensed current feedback signal which is proportional to the sensed electrode current;
   means for sensing voltage provided to the electrodes of the drug delivery device, the voltage sensing means generating a sensed voltage feedback signal which is proportional to the sensed electrode voltage;
   means coupled to the current sensing means for comparing the sensed current feedback signal with a predetermined current threshold signal and generating a current state signal in response to the comparison thereof;
   feedback signal selector means, the feedback signal selector means being responsive to at least the current state signal and receiving at least the sensed current feedback signal and sensed voltage feedback signal and generating a feedback signal corresponding to at least one of the sensed current feedback signal and the sensed voltage feedback signal in response to at least the current state signal;
   setpoint selector means, the setpoint selector means receiving a preselected voltage limit signal and preselected desired drug delivery current signal and being responsive to at least the current state signal, the setpoint selector means generating a setpoint signal corresponding to at least one of the voltage limit signal and the desired delivery current signal in response to at least the current state signal; and
   means for subtracting the feedback signal from the setpoint signal, the subtracting means generating an error signal corresponding to the difference between the feedback signal and the setpoint signal;
   the voltage and current generating means being responsive to the error signal and adjusting at least one of the current and voltage provided to the electrodes in response thereto.

20. A combination as defined by claim 19, wherein the adjustable voltage and current generating means includes a variable pulse generator and a pulse to power converter coupled to the variable pulse generator, the variable pulse generator being responsive to the error signal and generating a pulsed output signal which varies in correspondence to the error signal, the pulse to power converter being responsive to the output signal of the variable pulse generator and generating an output voltage which varies in correspondence to the pulse generator output signal.

21. A combination as defined by claim 19, wherein the electronic circuit further comprises:
   multiplication means, the multiplication means receiving the sensed current feedback signal and the sensed voltage feedback signal and effectively multiplying the sensed current feedback signal and sensed voltage feedback signal together and generating a sensed power feedback signal in response to the multiplication thereof, the sensed power feedback signal being provided to the feedback signal selector means; and
   means coupled to the multiplication means for comparing the sensed power feedback signal with a predetermined first power limit signal and generating a power state signal in response to the comparison thereof;
   wherein the feedback signal selector means is responsive to one of the current state signal and the power state signal, the feedback signal generated by the feedback signal selector means corresponding to one of the sensed current feedback signal, the sensed voltage feedback signal and the sensed power feedback signal in response to one of the current state signal and the power state signal;
   and wherein a preselected second power limit signal is provided to the setpoint selector means, the setpoint selector means being responsive to one of the current state signal and the power state signal, the setpoint signal generated by the setpoint selector means corresponding to one of the voltage limit signal, the desired delivery current signal and the second power limit signal in response to one of the current state signal and the power state signal.

22. A combination as defined by claim 19, wherein the electronic circuit further comprises:
   output enable switch means, the output enable switch means being coupled to the circuit in series between one of the electrodes of the drug delivery device and the voltage and current generating means, the output enable switch means being responsive to a dose state signal and selectively interrupting current flow provided to said one of the electrodes in response thereto; and total drug dose sensing means, the total drug dose sensing means receiving a predetermined total dose signal and comparing the total dose signal with a signal substantially representative of the quantity of drug administered to the patient by the drug delivery device and generating the dose state signal in response to the comparison thereof.

23. A combination as defined by claim 22, wherein the total drug dose sensing means includes:

means for determining the quantity of current over time provided to the electrodes of the drug delivery device, the current quantity determining means providing an accumulated current signal in response thereto, the accumulated current signal being the signal substantially representative of the quantity of drug administered to the patient by the drug delivery device; and means coupled to the current quantity determining means for comparing the accumulated current signal with the total dose signal and generating the dose state signal in response to the comparison thereof.

24. A combination as defined by claim 19, wherein the electronic circuit further comprises:

output enable switch means, the output enable switch means being coupled to the circuit in series between one of the electrodes of the drug delivery device and the voltage and current generating means, the output enable switch means being responsive to an excess current limit signal and selectively interrupting current flow provided to said one of the electrodes in response thereto; and means for comparing the sensed current feedback signal with a predetermined excess current threshold signal and generating the excess current limit signal in response to the comparison thereof.

25. A combination as defined by claim 19, wherein the adjustable voltage and current generating means includes a power amplifier circuit, the power amplifier circuit being responsive to the error signal and generating an output voltage which varies in correspondence to the error signal, the output voltage being provided to the electrodes of the drug delivery device.

26. A combination as defined by claim 19, wherein the adjustable voltage and current generating means includes a variable pulse generator, the variable pulse generator being responsive to the error signal and generating a pulsed output voltage which varies in correspondence to the error signal, the pulsed output voltage being provided to the electrodes of the drug delivery device.

* * * * *

UNITED STATES PATENT AND TRADEMARK OFFICE
CERTIFICATE OF CORRECTION

PATENT NO. : 5,246,418
DATED : September 21, 1993
INVENTOR(S) : Haynes, et al.

It is certified that error appears in the above-indentified patent and that said Letters Patent is hereby corrected as shown below:

Title page: item [54], now reads: "Iontophresis" and should read: --Iontophoresis--;

Column 6, line 48, now reads: "Value" and should read: --value--;

Column 7, line 9, now reads: "constant o current", and should read: --constant current--;

Column 7, line 12, now reads: "signals on passed", and should read: --signals on the three inputs of the set point selector circuit 50 will be passed--;

UNITED STATES PATENT AND TRADEMARK OFFICE
CERTIFICATE OF CORRECTION

PATENT NO. : 5,246,418
DATED : September 21, 1993
INVENTOR(S) : Haynes, et al.

Page 2 of 2

It is certified that error appears in the above-indentified patent and that said Letters Patent is hereby corrected as shown below:

Column 7, line 38, now reads: "delivery o device", and
should read: --delivery device--;

Column 15, line 65, now reads: "claim further", and
should read: --Claim 11, further--.

Signed and Sealed this

Fifth Day of September, 1995

Attest:

BRUCE LEHMAN

*Attesting Officer*     *Commissioner of Patents and Trademarks*